United States Patent [19]

Volke

[11] Patent Number: 4,743,499

[45] Date of Patent: May 10, 1988

[54] HYDROCOLLOID LAMINATE

[75] Inventor: Robert W. Volke, Garrettsville, Ohio

[73] Assignee: Variseal Corporation, Parkman, Ohio

[21] Appl. No.: 51,591

[22] Filed: May 20, 1987

[51] Int. Cl.⁴ .................. B32B 3/26; B32B 9/00; A61L 15/00

[52] U.S. Cl. .................. 428/317.3; 128/156; 428/319.3; 428/319.9; 428/343; 428/354; 428/355

[58] Field of Search ............ 128/156; 428/317.1, 428/317.3, 317.7, 319.3, 319.7, 319.9, 343, 354, 355; 604/336, 344, 369

[56] References Cited

U.S. PATENT DOCUMENTS

| | | | |
|---|---|---|---|
| 3,339,546 | 9/1967 | Chen | 128/156 |
| 3,536,072 | 10/1970 | Quelle | 128/169 |
| 3,645,835 | 2/1972 | Hodgson | 428/195 |
| 3,648,692 | 3/1972 | Wheeler | 128/156 |
| 3,908,645 | 9/1975 | Sandvig | 128/97 |
| 3,972,328 | 8/1976 | Chen | 128/156 |
| 4,253,460 | 3/1981 | Chen et al. | 128/156 |
| 4,427,737 | 1/1984 | Cilento et al. | 428/317.3 |
| 4,538,603 | 9/1985 | Pawelchak et al. | 128/156 |
| 4,551,490 | 11/1985 | Doyle et al. | 524/22 |
| 4,650,817 | 3/1987 | Allen, Jr. et al. | 428/317.1 |
| 4,655,210 | 4/1987 | Edenbaum et al. | 128/156 |

Primary Examiner—William J. Van Balen
Attorney, Agent, or Firm—Reese Taylor

[57] ABSTRACT

A hydrocolloid laminate (10) useful as a wound dressing. The laminate product comprises a lower layer of hydrocolloid adhesive (11), an upper layer of flexible open-cell polymer foam (12), first film layer (13) interposed between the adhesive layer and the foam layer and second film layer (14) provided on the foam layer on the side (17) opposite the first film layer.

7 Claims, 1 Drawing Sheet

HYDROCOLLOID LAMINATE

TECHNICAL FIELD

The present invention is directed toward an improved wound dressing material for medical use. Such dressings can be utilized in the hospital following surgery or to protect areas of the body that have been injured. The dressing can also be utilized by the patient in a non-hospital environment and, indeed, for dressing any wound or skin eruption regardless of the cause. The dressing comprises a laminate which provides adhesion and cushioning protection. The dressing may also be utilized to dispense medication to the wound site.

BACKGROUND ART

Representative art can be found in the area of wound dressings and ostomy sealing materials. Generally, it is known to combine an adhesive material with a plastic layer or film or with a foam layer or both. U.S. Pat. No. 3,339,546 for instance is directed toward a bandage which comprises a waterproof film such as polyethylene and a water swellable hydrocolloid adhesive.

U.S. Pat. No. 3,536,072 is directed toward a traction strip or tape for wrapping and immobilizing a limb that has been set. The strip includes a polyester outer layer, a middle sponge layer and an inner pressure sensitive adhesive layer.

U.S. Pat. No. 3,645,835 provides pressure sensitive adhesives that are permeable to moisture for use on skin and nails. The adhesive carries a single layer of backing material formed by a synthetic polymer and non-permeable to water.

U.S. Pat. No. 3,648,692 discloses surgical dressings comprising a layer of reticulated open-cell foam and a backing material that is nonabsorbent and liquid impermeable but gas permeable.

U.S. Pat. No. 3,908,645 is directed toward an ophthalmic pressure bandage including an elastomeric backing, a pressure sensitive layer attached to the backing and a multilayer pad attached to the opposite side. The pad provides a tri-layered composite including a resilient foam, an interlayer of absorbent, non-woven web and a porous, non-adherent facing such as polyethylene.

U.S. Pat. No. 3,972,328 is directed toward a bandage comprising an adhesive layer, a layer of flexible, semi-open cell polymeric foam and an outer water impervious flexible polymeric film coating.

Lastly, U.S. Pat. No. 4,538,603 provides a dressing material for treating skin lesions utilized with a granular material which interacts with wound exudate. The dressing includes one or two adhesive layers, a polymeric foam bonded thereto and an outer polymeric film or skin formed on top of the foam layer.

Although the art thus contains a variety of products and compositions that adhere directly to the body of a patient or affix medical implements thereto, none have suggested a laminate product that is crushable and resistant to permanent deformation.

SUMMARY OF THE INVENTION

It is therefore an object of the present invention to provide a laminate product for use as a wound dressing for application to skin.

It is another object of the present invention to provide a laminate product employing a hydrocolloid adhesive and a foam layer as a cushion which carries a layer of polymeric film on both sides.

It is another object of the present invention to provide a wound dressing that can dispense medication to the wound site over extended periods.

These and other objects of the present invention together with the advantages thereof over the prior art forms, which will become apparent from the following specification are accomplished by means hereinafter described and claimed.

In general, a hydrocolloid laminate according to the present invention comprises a lower layer of hydrocolloid adhesive, an upper layer of flexible open-cell polymer foam, first film layer interposed between the adhesive layer and the foam layer and second film layer provided on the foam layer on the side opposite the first film layer.

PREFERRED EMBODIMENT FOR CARRYING OUT THE INVENTION

Figure 1:
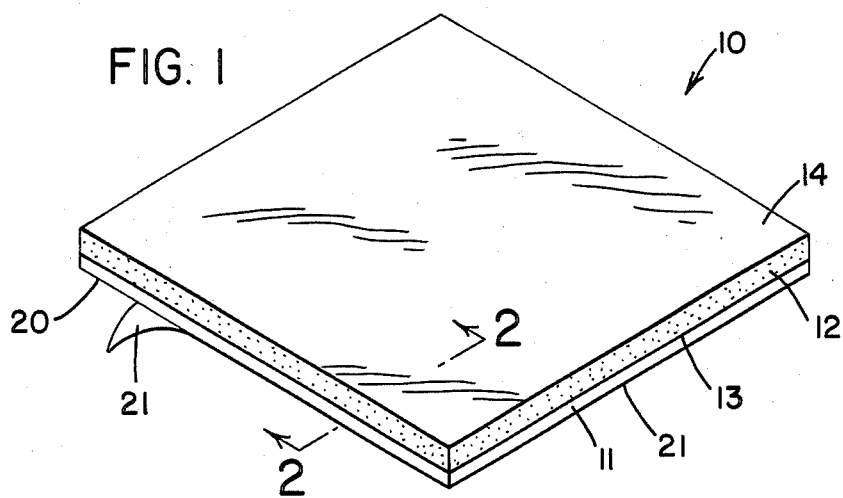
FIG. 1 is a perspective view of the laminate of the present invention.
Figure 2:
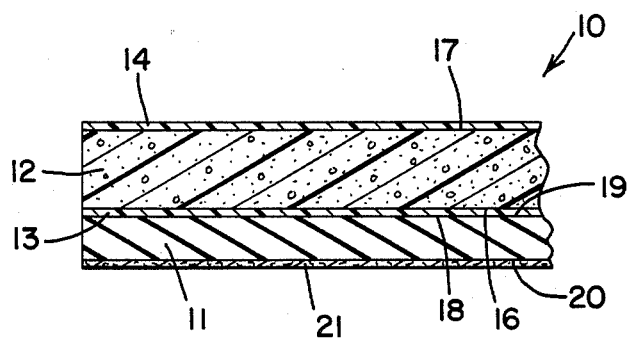
FIG. 2 is a section taken substantially along the line 2—2 of FIG. 1, of the laminate of the present invention.

The hydrocolloid laminate of the present invention is referred to generally by the numeral 10. The laminate comprises a hydrocolloid adhesive layer 11; an open-cell polymer foam or sponge layer 12; a first polymeric film layer 13 interposed between the hydrocolloid adhesive layer 11 and foam layer 12 and a second polymeric film layer 14 bonded to the upper surface of foam layer 12 which forms a protective skin or coating.

The composition of the hydrocolloid adhesive layer 11 comprises polyisobutylene rubber; a water soluble hydrocolloid gum; fiber reinforcement and mineral oil. Pigments such as titanium dioxide are optional depending upon the desired appearance or color of the final composition. A general disclosure of useful hydrocolloid adhesives is found in U.S. Pat. No. 4,551,490, the subject matter of which is incorporated herein by reference. The polyisobutylene rubber employed, for instance, has a low molecular weight, on the order of from about 36,000 to about 58,000 (Florey). Such polyisobutylenes are commercially available under the trademark VISTANEX from Exxon as grades LM-MS and LM-MH.

Optionally, in order to increase the elasticity, tear resistance, and cohesiveness of the adhesive compositions as indicated by a reduction in the cold flow of the adhesive composition, an elastomeric polymer such as butyl rubber can be blended with the polyisobutylenes. Butyl rubber is a copolymer of isobutylene with a minor amount of isoprene having a viscosity average molecular weight of from about 350,000 to about 450,000 (Florey). The polyisobutylenes and butyl rubber can be blended together on a weight basis of from about 4 parts polyisobutylene to about 1 part butyl rubber to about 1 part polyisobutylene to about 4 parts butyl rubber with about 1 part low molecular weight polyisobutylene to about 2 parts butyl rubber being preferred.

The hydrocolloid gums are water swellable or water soluble compounds such as sodium carboxymethylcellulose, pectin, and various natural gums. A general disclosure of suitable materials is also found in U.S. Pat. No. 4,551,490. The fiber reinforcement is preferably a water swellable material which performs the dual function of absorbing liquids and strengthening the hydrocolloid. A disclosure of these also is provided in the aforementioned U.S. Pat. No. 4,551,490.

The adhesive composition is prepared as described in the aforementioned U.S. Pat. No. 4,551,490. The resultant composition is then extruded into continuous sheets having a thickness of about 50 mils (1.3 mm). In order to extrude this thin a layer and avoid defects, the extrusion apparatus described in my copending application Ser. No. 855,716, filed Apr. 25, 1986, now US. Pat. No. 4,693,858 is preferred. The present invention is not limited to manufacture with such equipment; however, with some other apparatus, the hydrocolloid adhesive layer may have a greater thickness, such as up to about 80 mils (2 mm).

The polymeric foam layer 12 should be a totally open-cell structure such as a flexible polyurethane foam. If desired, the foam layer can be impregnated with medication for preventative as well as therapeutic purposes. The release of the medication will be determined, in part, by the permeability of the film layer 13. A suitable thickness for the foam layer ranges between about 20 to 80 mils (0.5 to 2 mm) with 60 mils (1.5 mm) being preferred.

During manufacture of the laminate product 10, one side 16 of the foam layer 12 receives a polymeric film layer 13 which can be permeable or impermeable again, depending upon the desired movement of moisture into the foam layer and movement of medication therefrom. The other side 17 also receives a polymeric film layer 14 which is preferably impermeable or only semipermeable. Suitable polymers for both films include polyurethane and syndiotactic 1,2-polybutadiene. The films can be the same or different composition and thickness, the latter ranging between about 0.5 to 1.5 mils (0.01 to 0.04 mm) with 0.7 mils (0.02 mm) preferred.

They can be affixed to the foam layer 12 by any suitable means including the use of solvents or adhesives. Preferably and conveniently the films can be heat bonded to the foam layer 12 as is known in the art, thereby avoiding the use of separate adhesives.

Final manufacture requires the lamination of the foregoing film-foam-film product to the hydrocolloid 11. To do so, the underside 18 of film layer 13 is affixed directly to the hydrocolloid adhesive layer 11 by removal of the treated paper coating from upper side 19 of the adhesive layer 11. The paper (not shown) is customarily applied to the upper and under sides, 19 and 20, respectively, of hydrocolloid adhesives during manufacture for protection of the surfaces. The film 13 and hydrocolloid adhesive 11 are pressed together sufficiently to form a bond. The foregoing steps can be conducted manually or in an automated fashion, employing suitable equipment. Overall thickness of the laminate 10 is from about 60 to 150 mils (1.5 to 3.8. mm).

In the event the desired hydrocolloid 11 lacks sufficient tack to adhere to the film layer 13, a transfer adhesive can be employed. Suitable adhesives are acrylic-based and can be separately applied to the hydrocolloid surface 19 or the underside 18 of film layer 13, either of which is covered with release paper until ready for application.

Generally, large sheets of the laminate product are formed from which the desired product sizes can be die cut. The under side 20 of the hydrocolloid adhesive layer will also contain a layer of treated paper 21 which is removed for end use by the patient or attending medical personnel.

The laminate product of the present invention differs from the known laminate structures in that it employs an open-cell polymer foam and the inner film layer 13. Without the inner film layer, the application of pressure to the outer film 14 would compress the foam layer and, because of its open-cell structure, the outer film would adhere to the hydrocolloid layer 11. The foam layer, lacking the resilience to expand against the adhesive forces holding the hydrocolloid adhesive and outer film 14 layers together, would remain permanently collapsed leaving dimples and diminished foam protection. Indeed, if large areas were involved, such as by the patient laying on the laminate or otherwise applying weight thereto, the total cushioning effect over the entire area would be lost.

As will now be appreciated, when the inner film 13 is employed, the foam can repeatedly be crushed against the patient's body and against the hydrocolloid adhesive layer and in every instance it will spring back to its original form within a matter of several seconds. Thus, the cushioning effect is not lost.

As an example of the present invention, a hydrocolloid adhesive formulation was prepared extruded to a thickness of 60 mils (1.5 mm). A polyurethane foam, having 80 pores per inch (ppi) and 60 mils thick (1.5 mm) was covered on one side with polyurethane film, 0.7 mils (0.02 mm) thick and on the other side with syndiotactic 1,2-polybutadiene, 0.75 mils (0.02 mm) thick. The first side was then pressed evenly against the hydrocolloid layer.

Test squares, approximately 4 inches (10 cm) per side were cut and subjected to pressure tests by applying pressure to local points (finger pressure) and by crushing the entire square between flat surfaces. Upon removal of the pressure, the hydrocolloid laminate returned to its original thickness within one second.

Based upon the foregoing disclosure, it should now be apparent that the hydrocolloid laminate described herein fulfills the objects set forth hereinabove. It should also be apparent to those skilled in the art that the hydrocolloid laminate of the subject invention can be employed in a variety of medical uses and sizes so as to accommodate wound dressings and the like.

Moreover, a variety of components can be selected for the four layers described herein. It is thus to be understood that any variations evident fall within the scope of the claimed invention; therefore, the selection of specific materials and component elements can be determined without departing from the spirit of the invention herein disclosed and described. Moreover, the scope of the invention shall include all modifications and variations that may fall within the scope of the attached claims.

I claim:

1. A hydrocolloid laminate comprising:
a lower layer of hydrocolloid adhesive;
an upper layer of flexible open-cell polymer foam;
first film layer interposed between said adhesive layer and said polymer foam layer; and
second film layer provided on said polymer foam layer on the side opposite said first film layer.

2. A hydrocolloid laminate, as set forth in claim 1, wherein said polymer foam comprises polyurethane.

3. A hydrocolloid laminate, as set forth in claim 1, wherein said first film layer comprises polyurethane.

4. A hydrocolloid laminate, as set forth in claim 1, wherein said first film layer comprises syndiotactic 1,2-polybutadiene.

5. A hydrocolloid laminate, as set forth in claim 1, wherein said second film layer comprises polyurethane.

6. A hydrocolloid laminate, as set forth in claim 1, wherein said second film layer comprises syndiotactic 1,2-polybutadiene.

7. A hydrocolloid laminate, as set forth in claim 1, further comprising a pressure sensitive adhesive layer between said first film layer and said polymer foam layer.

* * * * *